United States Patent [19]

Hertler

[11] Patent Number: 5,072,029
[45] Date of Patent: Dec. 10, 1991

[54] CATALYZED PROCESS FOR REACTING CARBOXYLIC ACIDS WITH VINYL ETHERS

[75] Inventor: Walter R. Hertler, Kennett Square, Pa.

[73] Assignee: E. I. Du Pont de Nemours and Company, Wilmington, Del.

[21] Appl. No.: 507,349

[22] Filed: Apr. 10, 1990

[51] Int. Cl.$^5$ .............................................. C07C 69/52
[52] U.S. Cl. .................................. 560/225; 560/113; 560/224; 560/240; 560/261; 549/427; 549/499
[58] Field of Search ............... 560/225, 113, 224, 261; 1/240; 549/427, 499

[56] References Cited

FOREIGN PATENT DOCUMENTS 0176238 2/1986 European Pat. Off. .

OTHER PUBLICATIONS

CA 77(17) 114148z 1972.
CA 108(23) 204195a 1988.

Primary Examiner—Paul J. Killos

[57] ABSTRACT

The present invention relates to a process for the reaction of carboxylic acids with vinyl ethers using a non-polymeric pyridine hydrochloride and/or polymeric vinylpyridine hydrochloride as a catalyst.

29 Claims, No Drawings

CATALYZED PROCESS FOR REACTING CARBOXYLIC ACIDS WITH VINYL ETHERS

BACKGROUND OF THE INVENTION

Field of the Invention

This invention concerns an improved process for the reaction of carboxylic acids with vinyl ethers such as 3,4-dihydro-2H-pyran (dihydropyran) using monomeric and polymeric pyridine hydrochloride catalysts to produce acetal esters. The structure of the polymeric catalyst is a crosslinked poly 2-, 3-, or 4-vinylpyridine hydrochloride. The non-polymeric catalyst is a hydrochloride of pyridine or an alkyl-substituted pyridine with no more than one alkyl substituent in positions 2 and 6.

The prior art catalysts for the reaction of carboxylic acids with vinyl ethers to produce acetal esters have been strong acids such as sulfuric, hydrochloric and p-toluenesulfonic acid. The advantage of the monomeric and polymeric pyridine hydrochloride catalysts is that they are milder than the strong acids, allow better control of the reaction, and avoid the high corrosiveness of the stronger acids. The present invention is useful as a clean, commercially feasible method for synthesizing tetrahydropyranyl acrylate and methacrylate which are useful in photoresist and other applications.

Background Art

U.S. Pat. No. 4,212,814 (Schonberger) teaches a "one-pot" process for the preparation of "Florafur" by reacting 2,3-dihydrofuran with water in the presence of a catalytic amount of acidic catalyst conducted at a pH below 2.5 followed by reacting the product with 5-fluoro-uracil in the presence of a Friedel Crafts-type catalyst. Example 7 uses a polymeric sulfonic acid to catalyze the addition of water to 2,3-dihydrofuran to produce bis-2-furanidyl ether.

C. R. Marston, P. E. Krieger, G. L. Goe, *Synthesis*, 1988, 393 disclose polymeric pyridine hydrochloride as a useful catalyst for addition of alcohols and phenols to dihydropyran.

R. Raussen et al., *J. Org. Chem.*, 1966, 31. 26 disclose pyridine hydrochloride as a superior (to p-toluenesulfonic acid) catalyst for ketalization of a steroidal ketone with ethylene glycol.

J. Yoshida, J. Hashimoto, N. Kawabata, *Bull. Chem. Soc. Jap.*, 1981, 54, 309 discusses advantages of crosslinked polyvinyl pyridine hydrochloride as a mild catalyst for acetalization of carbonyl compounds with ethylene glycol and esterification of carboxylic acids with alcohols.

The present invention improves upon prior art processes by using a monomeric pyridine hydrochloride or polymer-supported pyridine hydrochloride [crosslinked poly(vinylpyridine hydrochloride)] to catalyze the reaction of RCOOH with vinyl ethers such as 3,4-dihydro-2H-pyran (dihydropyran).

SUMMARY OF THE INVENTION

The present invention concerns an improved process for the catalyzed reaction of carboxylic acids with vinyl ethers (e.g. dihydropyran) that uses a polymeric pyridine hydrochloride salt of a crosslinked poly (2-, 3-, and/or 4-vinylpyridine hydrochloride) structure.

A second embodiment of the invention uses non-polymeric catalysts which comprise hydrochlorides of pyridine and/or alkyl substituted ($C_1$–$C_4$) pyridines with no more than one alkyl substituent in positions 2 and 6.

DETAILED DESCRIPTION OF THE INVENTION

The present invention is an improved process for the acid catalyzed reaction of carboxylic acids with vinyl ethers.

Vinyl ethers that will work in the process are of the structure

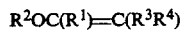

$$R^2OC(R^1)\!=\!C(R^3R^4)$$

wherein
$R^1$ is hydrogen or $C_1$–$C_6$ alkyl;
$R_2$ is a $C_1$–$C_{12}$ alkyl; and
$R_3$ and $R_4$ independently are hydrogen or $C_1$–$C_6$ alkyl where the definition of alkyl includes the joining of $R^1$ and $R^2$ or $R^1$ and either $R^3$ or $R^4$, or $R^2$ and either $R^3$ or $R^4$ to form a 5-, 6- or 7-membered ring.

Examples of operable vinyl ethers include but are not limited to those in Examples 1–4 and methyl vinyl ether, propyl vinyl ether, isopropenyl methyl ether and 1-methoxycyclohexene. The preferred vinyl ether for this process is 3,4-dihydro-2H-pyran (dihydropyran).

The carboxylic acids (RCOOH) that may be used are those where R may be (optionally substituted) alkyl, alkaryl, alkenyl, aryl and aralkyl. The carboxylic acid may be monomeric or polymeric. Examples in addition to those exemplified in the case are:

benzoic acid
acetic acid
m-chlorobenzoic acid
poly(methacrylic acid)
poly(acrylic acid)
styrene-4-carboxylic acid
poly(styrene-4-carboxylic acid)
2-naphthalenecarboxylic acid
phthalic acid Preferred carboxylic acids for use in the process are methacrylic acid and acrylic acid.

The catalysts used in the instant process are polymeric and non-polymeric pyridine hydrochlorides. The structure of the polymeric hydrochloride catalyst is a crosslinked poly (2-, 3-, or 4-vinylpyridine hydrochloride). The non-polymeric catalysts are hydrochlorides of pyridine and alkyl substituted pyridine ($C_1$ to $C_4$ alkyl) having no more than one alkyl substituent in positions 2 and 6. A preferred polymeric catalyst is poly(4-vinylpyridine hydrochloride). A preferred non-polymeric catalyst is pyridine hydrochloride.

Hydrobromides might also be used as catalysts in the present process but are not preferred for most reactions due to their corrosiveness.

In a preferred process, the catalyst is used without solvent other than the vinyl ether used in the reaction. However it may be necessary to use a solvent to solubilize the polymer acid reactant in certain cases. The solvent should be non-basic and aprotic. Solvents such as, but not limited to hydrocarbons, chlorinated hydrocarbons, ketones and ethers may be used. Amines, alcohols and acetic acid should be avoided.

Reaction temperatures for the process may be from about ambient to about 110° C. Higher temperatures disfavor product formation. It is convenient to carry out the reaction at the boiling point of the vinyl ether (or of any solvent, if used).

The catalyst may be used at levels of from about 20 mole % to about 0.1 mole % of carboxylic acid undergoing reaction.

The ratio of vinyl ether to carboxylic acid should be greater than or equal to one.

EXAMPLES

EXAMPLE 1

Preparation of 2-tetrahydropyranyl methacrylate with crosslinked poly(vinylpyridine hydrochloride) catalyst.

A mixture of 20 mL (220 mmol) of 3,4-dihydro-2H-pyran, 8.48 mL (100 mmol) of methacrylic acid, 3 g of crosslinked poly(4-vinylpyridine hydrochloride) (Fluka Chemical Corp., catalog number 82803, about 6 meq/g), and 0.25 g of phenothiazine was heated at 55° C. for 18 hours. After cooling to room temperature, the mixture was filtered to remove the polymeric catalyst. $^1$H NMR analysis of the filtrate showed the presence of dihydropyran and 2-tetrahydropyranyl methacrylate. No methacrylic acid was observed. Thus, the conversion was nearly quantitative. The product was purified by removal of the excess dihydropyran under reduced pressure followed by distillation of the tetrahydropyranyl methacrylate over calcium hydride, phenothiazine, and diphenylpicryl hydrazyl at 37° C. (0.5 mm)–45° C. (0.6 mm).

EXAMPLE 2

Preparation of 2-tetrahydropyranyl acrylate with crosslinked poly(vinylpyridine hydrochloride) catalyst.

A mixture of 310 mL (2.75 mol) of 3,4-dihydro-2H-pyran, 99.1 g (94 mL, 1.38 mol) of acrylic acid, 5 g of crosslinked poly(4-vinylpyridine hydrochloride) (Fluka Chemical Corp., catalog number 82803, 6 meq/g), and 0.5 g of phenothiazine was warmed until an exothermic reaction caused the temperature to rise to 99° C. An ice bath was used to cool the mixture to 65° C., and the mixture was stirred at 65° C. for 18 hours. After cooling to room temperature, the mixture was filtered to remove the catalyst. NMR analysis of the filtrate showed the presence of 2-tetrahydropyranyl acrylate and 3,4-dihydro-2H-pyran with little or no acrylic acid. The mixture was stirred with anhydrous sodium carbonate and calcium hydride for 1 hour. After removal of excess 3,4-dihydro-2H-pyran in a rotary evaporator, distillation over calcium hydride, anhydrous sodium carbonate, and phenothiazine gave 136.6 g of 2-tetrahydropyranyl acrylate, b.p. 66°–70° C. (3.2 mm).

EXAMPLE 3

Preparation of 1-ethoxy-1-propyl methacrylate with crosslinked poly(vinylpyridine hydrochloride) catalyst.

Using the procedure of Example 2, a mixture of 116 g (114 mL, 1.35 mol) of methacrylic acid and 236 g (304 mL, 2.7 mol) of ethyl 1-propenyl ether was converted to 1-ethoxy-1-propyl methacrylate, b.p. 24°–27° C. (0.2 mm).

$^1$H NMR (360 MHz, CDCl$_3$): 0.95 (t, J=7.5 Hz, 3H, CH$_3$), 1.22 (t, J=7 Hz, 3H, CH$_3$), 1.76 (m, J=7, 1 Hz, 2H, CH$_2$), 1.96 (m, 3H, =CCH$_3$), 3.57 (m, 1H, OCH$_2$), 3 74 (m, 1H, OCH$_2$), 5.60 (m, 1H, —CH), 5.84 (t, J=6 Hz, 1H, OCHO), 6.16 (m, 1H, =CH).

EXAMPLE 4

Preparation of 1-isobutoxy-1-ethyl methacrylate with crosslinked poly(vinylpyridine hydrochloride) catalyst.

Using the procedure of Example 2, a mixture of 300.5 g (391 mL, 3 moles) of isobutyl vinyl ether and 129.1 g (127 mL, 1.5 moles) of methacrylic acid was converted to 1-ethoxy-1-propyl methacrylate, b.p. 48.5° C. (2.2 mm).

$^1$H NMR (360 MHz, CDCl$_3$): 0.90 (d, J=6 Hz, 3H, Me),
0.91 (d, J=6 Hz, 3H, Me), 1.44 (d, J=5 Hz, 3H, Me), 1.84 (m, 1H, =CHMe$_2$), 1.95 (t, 1 Hz, 3H, MeC=C), 3.26
(dd, J=7, 10 Hz, 1H, OCH$_2$), 3.44 (dd, J=7, 10 Hz, 1H,
OCH$_2$), 5.59 (m, 1H, CH=C), 5.96 (q, J=5 Hz, 1H, OCHO), 6.15 (m, 1H, CH=C).

Analysis Calculated for C$_{10}$H$_{18}$O$_3$:
C, 64.49; H, 9.74.
Found:
C, 65.34; H, 9.69.

EXAMPLE 5

Preparation of 2-tetrahydrofuranyl methacrylate with crosslinked poly(vinylpyridine hydrochloride) catalyst.

A mixture of 4.97 g of crosslinked poly(4-vinylpyridine hydrochloride) (Fluka Chemical Corp., catalog number 82803, 6 meq/g), 192 g (207 mL, 2.74 mol) of 2,3-dihydrofuran, 118 g (116 mL, 1.36 mol) of methacrylic acid, and 1 g of phenothiazine was heated at 2° C. per minute. When the temperature reached 45° C., an exothermic reaction caused the temperature to rise to 82° C. The catalyst was removed by filtration. NMR analysis of the filtrate showed no residual methacrylic acid. After addition of sodium carbonate and calcium hydride, excess dihydrofuran was removed with a rotary evaporator, and distillation gave 151.7 g of tetrahydrofuranyl methacrylate, b.p. 43°–44° C. (0.75 mm).

$^1$H NMR (300 MHz, CDCl$_3$): 1.93 (m, 3H, MeC=C), 1.95–2.1 (m, 4H, CH$_2$), 3.95 (m, 1H, OCH$_2$), 4.08 (m, 1H, OCH$_2$), 5.58 (m, 1H, C=CH), 6.1 (s, 1H, OCHO),
6.38 (m, J=7, 1H, C=CH).

EXAMPLE 6

Reaction of dihydropyran with poly(styrene, maleic anhydride, isopropyl hydrogen maleate) in the presence of pyridine hydrochloride catalyst.

A 5 g sample of poly(styrene [50 mol %], isopropyl hydrogen maleate [32 mol %], maleic anhydride [18 mol %]) was suspended in 75 mL of 3,4-dihydro-2H-pyran and treated with 0.1 g of pyridine hydrochloride. The mixture was stirred at reflux for 18 hours, during which time a homogeneous solution was formed. After cooling to room temperature, the solution was stirred for 1 hour with crosslinked poly(dimethylaminomethylstyrene) to remove the catalyst. After filtration, the product was isolated from the filtrate by precipitation in methanol and dried to give 3 g of poly(styrene, isopropyl tetrahydropyranyl maleate, maleic anhydride). Titration of the starting material with 0.1N sodium hydroxide shows 4.32 meq/g of anhydride and acid. Titration of the product shows 2.49 meq/g of anhydride. IR analysis of the product shows absorption characteristic of anhydride (1855 and 1780 cm$^{-1}$), but no absorption characteristic of carboxylic acid. Differential scanning calorimetry (DSC) of the product shows a sharp decomposition endotherm peaking at 153.9° C. (104.1 J/g) which is absent from the starting material. Thermal gravimetric analysis (TGA) shows a 13.36% weight loss centered at 154.54° C. which is not seen in the TGA of the starting material. The thermal event at 154° C. is the thermal loss of dihydropyran to form polymeric carboxylic acid groups.

EXAMPLE 7

Reaction of dihydropyran with poly(styrene, methyl acrylate, acrylic acid) in the presence of pyridine hydrochloride catalyst.

Using the procedure of Example 6, reaction of 10 g of poly(styrene [55 wt %], methyl acrylate [20 wt %], acrylic acid [25 wt %]) (Joncryl 67), 125 mL of 3,4-dihydro-2H-pyran, and 0.1 g of pyridine hydrochloride gave 10 g of poly(styrene, methyl acrylate, tetrahydropyranyl acrylate) after precipitation from dichloromethane in methanol at −70° C. $^1$H NMR (360 MHz, THF-d$_8$): 5.9 (OCHO of tetrahydropyranyl ester). Mole ratio of styrene to tetrahydropyranyl ester=1.8:1. GPC: Mn=6260, Mw=15,900, Mw/Mn=2.54. DSC: Tg=52° C., decomposition endotherm peak at 180.77° C. (125.4 J/g). TGA: 20.69% weight loss at about 180° C. Titration of the product with 0.1N sodium hydroxide shows the presence of 0.2 meq/g of residual carboxylic acid groups. Titration of the starting material shows 3.4 meq/g of carboxylic acid.

EXAMPLE 8

Reaction of dihydropyran with poly(styrene, benzyl tetrahydropyranyl maleate) in the presence of pyridine hydrochloride catalyst.

Poly(styrene [50 mol %], benzyl hydrogen maleate [50 mol %]) was prepared by stirring at reflux for 25 hours a mixture of poly(styrene [50 mol %], maleic anhydride [50 mol %]), 200 mL of benzyl alcohol and 400 mL of THF. The THF was removed on a rotary evaporator, and the product was precipitated in hexane followed by precipitation from THF with diethyl ether to give 46 g of poly(styrene, benzyl hydrogen maleate). A mixture of 25 g of poly(styrene, benzyl hydrogen maleate), 150 mL of 3,4-dihydro-2H-pyran, and 0.5 g of pyridine hydrochloride was stirred at reflux 18 hours. THF was added to reduce the viscosity, and the mixture was stirred 1 hour with crosslinked poly(dimethylaminomethylstyrene). After filtration, the product was precipitated from the filtrate in methanol to give 29 g of poly(styrene, benzyl maleate, tetrahydropyranyl maleate). $^1$H HMR (360 MHz) shows the molar ratio of tetrahydropyranyl groups (δ 5.8 ppm) to benzyloxy groups (δ 5.0 ppm) to be about 4.4:1. Titration with 0.1N sodium hydroxide shows 0.09 meq/g of COOH groups. DSC: decomposition endotherm 140.75° C. TGA: 24.7% weight loss at 147.9° C.

It is to be understood that the scope of the present invention is not limited by the specific embodiments exemplified but as described in the appended claims.

What is claimed is:

1. A method of producing acetal esters which comprises reacting a vinyl ether with a carboxylic acid in the presence of a catalytic amount of polymer-supported pyridine hydrochloride.

2. The method of claim 1 wherein the polymer-supported pyridine hydrochloride is a crosslinked poly 2-, 3- or 4-vinylpyridine hydrochloride.

3. The method of claim 2 wherein the vinyl ether is selected from 3,4-dihydro-2H-pyran, isobutyl vinyl ether, methyl vinyl ether, isopropenyl methyl ether, propyl vinyl ether and 1-methoxycyclohexene.

4. The method of claim 2 wherein the vinyl ether is 3,4-dihydro-2H-pyran.

5. The method of claim 2 wherein the polymer-supported catalyst is crosslinked poly(4-vinylpyridine hydrochloride).

6. The method of claim 4 wherein the polymer-supported catalyst is crosslinked poly(4-vinylpyridine hydrochloride).

7. The method of claim 1 wherein the carboxylic acid is selected from maleic acid, methacrylic acid, acrylic acid, benzoic acid, acetic acid, m-chlorobenzoic acid, styrene-4-carboxylic acid, 2-naphthalenecarboxylic acid and phthalic acid.

8. The method of claim 2 wherein the carboxylic acid is methacrylic acid.

9. The method of claim 2 wherein the carboxylic acid is acrylic acid.

10. The method of claim 2 wherein the vinyl ether is isobutyl vinyl ether.

11. The method of claim 10 wherein the carboxylic acid is methacrylic acid.

12. The method of claim 1 conducted at a reaction temperature of about ambient temperature to about 110° C.

13. The method of claim 1 conducted in the presence of a solvent.

14. The method of claim 1 wherein the solvent is non-basic and aprotic.

15. The method of claim 1 wherein the catalyst is present at levels of from about 20 mole percent to about 0.1 mole percent of carboxylic acid undergoing reaction.

16. The method of claim 2 wherein the vinyl ether is 3,4-dihydro-2H-pyran, the carboxylic acid is methacrylic acid and the catalyst is poly(4-vinylpyridine hydrochloride).

17. The method of claim 2 wherein the vinyl ether is 3,4-dihydro-2H-pyran, the acid is acrylic acid and the catalyst is poly(4-vinylpyridine hydrochloride).

18. The method of claim 1 wherein the ratio of vinyl ether to carboxylic acid is greater than or equal to 1.

19. The method of claim 1 wherein the catalyst is removed by filtration.

20. The method of claim 19 wherein the product is removed by distillation.

21. A method for producing acetal esters which comprises reacting a vinyl ether with a carboxylic acid in the presence of a catalytic amount of a non-polymeric catalyst selected from pyridine hydrochloride and $C_1$ to $C_4$ alkyl substituted pyridine hydrochloride with no more than one $C_1$ to $C_4$ alkyl substituent in positions 2 and 6.

22. The method of claim 20 where the vinyl ether is selected from isobutyl vinyl ether, 3,4-dihydro-2H-pyran, methyl vinyl ether, propyl vinyl ether, isopropenyl methyl ether, and 1-methoxy cyclohexene.

23. The method of claim 22 wherein the vinyl ether is 3,4-dihydro-2H-pyran.

24. The method of claim 21 wherein the carboxylic acid is selected from poly(methacrylic acid), poly(acrylic acid), maleic acid, benzoic acid, acetic acid, m- chlorobenzoic acid, styrene-4-carboxylic acid, poly(styrene-4-carboxylic) acid, 2-naphthalenecarboxylic acid and phthalic acid.

25. The method of claim 24 wherein the carboxylic acid is selected from poly(methacrylic acid), poly(acrylic acid), and poly(styrene-4-carboxylic acid).

26. The method of claim 24 wherein the carboxylic acid is poly(acrylic acid).

27. The method of claim 21 wherein the vinyl ether is 3,4-dihydro-2H-pyran, the carboxylic acid is poly(methacrylic acid) and the catalyst is pyridine hydrohloride.

28. The method of claim 21 wherein the vinyl ether is 3,4-dihydro-2H-pyran, the carboxylic acid is poly(acrylic acid) and the catalyst is pyridine hydrochloride.

29. The method of claim 21 conducted in a non-basic and aprotic solvent.

* * * * *